(12) United States Patent
Jayaraman

(10) Patent No.: US 7,090,858 B2
(45) Date of Patent: Aug. 15, 2006

(54) COATED FILTER BAG MATERIAL FOR ORAL ADMINISTRATION OF MEDICAMENT IN LIQUID AND METHODS OF MAKING SAME

(76) Inventor: Swaminathan Jayaraman, 459 Lowell Pl., Fremont, CA (US) 94536

( * ) Notice: Subject to any disclaimer, the term of this patent is extended or adjusted under 35 U.S.C. 154(b) by 135 days.

(21) Appl. No.: 09/924,540

(22) Filed: Aug. 9, 2001

(65) Prior Publication Data
US 2003/0032945 A1    Feb. 13, 2003

(51) Int. Cl.
*A61K 9/00* (2006.01)
*A23F 5/00* (2006.01)
*A23F 3/00* (2006.01)

(52) U.S. Cl. .......... 424/400; 426/594; 426/597
(58) Field of Classification Search .......... 424/404, 424/415, 439, 443, 434; 53/445; 426/19, 426/20, 534, 79; 604/404, 408
See application file for complete search history.

(56) References Cited

U.S. PATENT DOCUMENTS

| | | | |
|---|---|---|---|
| 3,873,752 A | 3/1975 | Reymond et al. | 426/369 |
| 3,966,986 A | 6/1976 | Hunter et al. | 426/534 |
| 4,003,999 A | 1/1977 | Lybrand et al. | 424/195 |
| 4,055,668 A * | 10/1977 | Kopp | 426/79 |
| 4,076,847 A | 2/1978 | Johnson et al. | 426/78 |
| 4,153,153 A | 5/1979 | Herzog | 206/0.5 |
| 4,683,140 A | 7/1987 | Kang | 426/597 |
| 4,726,956 A | 2/1988 | Christie | 426/80 |
| 4,998,623 A | 3/1991 | Doull | 206/531 |
| 5,173,154 A | 12/1992 | Heinrich | 162/129 |
| 5,181,505 A | 1/1993 | Lew et al. | 128/200 |
| 5,203,459 A | 4/1993 | Wade | 206/572 |
| 5,222,940 A | 6/1993 | Wilk | 604/77 |
| 5,282,789 A | 2/1994 | Lundy | 604/55 |
| 5,322,700 A | 6/1994 | Drake et al. | 426/79 |
| 5,595,779 A | 1/1997 | Shimabukuro | 426/597 |
| 5,674,522 A | 10/1997 | Shah et al. | 424/439 |
| 5,718,681 A | 2/1998 | Manning | 604/56 |
| 5,723,453 A | 3/1998 | Phykitt | 514/165 |
| 5,736,144 A | 4/1998 | Gideon | 424/195.1 |
| 5,747,053 A | 5/1998 | Nashimoto et al. | 424/405 |
| 5,755,688 A | 5/1998 | Piontek et al. | 604/83 |
| 5,755,689 A | 5/1998 | Mazer et al. | 604/84 |
| 5,773,004 A | 6/1998 | Takahashi | 424/195.1 |
| 5,776,431 A | 7/1998 | Galat | 424/44 |
| 5,804,567 A | 9/1998 | Cheng et al. | 514/49 |
| 5,869,059 A | 2/1999 | Garza | 424/195.1 |
| 5,871,789 A | 2/1999 | Romagnoli | 426/77 |
| 5,888,527 A | 3/1999 | Nashimoto et al. | 424/405 |
| 5,908,401 A | 6/1999 | Henley | 604/20 |
| 5,910,308 A | 6/1999 | D'Jang | 424/195.1 |
| 5,921,955 A | 7/1999 | Mazer et al. | 604/83 |
| 5,927,052 A | 7/1999 | Nippes et al. | 53/445 |

(Continued)

FOREIGN PATENT DOCUMENTS

CN    1104036 A    *   6/1995

(Continued)

*Primary Examiner*—Lakshmi Channavajjala
(74) *Attorney, Agent, or Firm*—Fleit Kain Gibbons Gutman Bongini & Bianco; Paul D. Bianco; Martin Fleit (57) ABSTRACT

A coated filter bag for use in cold or hot drinks, in particular, a novel method for administration of pharmaceutical actives, supplemental nutrients, genetically derived materials, or other beneficial agents using a coated filter bag that includes at least one agent that solubilizes when in contact with liquid and is dispersed in the proper dosage amount into the liquid for oral consumption.

19 Claims, 5 Drawing Sheets

| U.S. PATENT DOCUMENTS | | | | JP | 53075346 | * | 7/1978 |
|---|---|---|---|---|---|---|---|
| 6,143,316 A | 11/2000 | Hayden et al. | 424/442 | JP | 9-108111 | | 4/1997 |

FOREIGN PATENT DOCUMENTS

| GB | 160414 | * | 11/1981 |
|---|---|---|---|

* cited by examiner

COATED FILTER BAG MATERIAL FOR ORAL ADMINISTRATION OF MEDICAMENT IN LIQUID AND METHODS OF MAKING SAME

FIELD OF THE INVENTION

The present invention relates to a method for administration of medicaments. In particular, the invention is directed to a coated filter bag for use in cold or hot drinks that includes at least one pharmaceutical active, supplemental nutrient, genetically derived material, or other beneficial agent. The agent solubilizes when in contact with liquid and is dispersed in the proper dosage amount into the liquid for oral consumption.

BACKGROUND OF THE INVENTION

There are a number of daily supplement or pharmaceutical agents, directed to the prevention or treatment of an assortment of medical issues. For example, it is well known that aspirin reduces the risk of heat disease and stroke and that a regular dose of anticoagulants and antiplatelets help to maintain a healthy concentration level of blood in the arteries. Other pharmaceuticals taken on a regular basis may include ace inhibitors, cholesterol and lipid reducing agents, and metabolism regulatory agents. The supplements or pharmaceutical agents can be administered using a variety of methods. The most popular and widely used method for daily intake of the pharmaceutical agent is to ingest a pill, tablet, or capsule containing the beneficial agent with a fluid to help dissolve the pill.

For those who have difficulty swallowing pills, however, such as in the case of infants, elderly persons, paralyzed persons, or severely injured persons, a variety of methods have been used, for example, pills or powdered medications crushed and mixed with food, such as apple sauce, covered spoon devices, medicated straws, and the like. A medicated delivery straw, as in U.S. Pat. No. 5,718,681, allows the dry medication to be loaded in a delivery tube, dissolved by the fluid taken into the tube, and ingested. U.S. Pat. No. 5,921,955 teaches a bottle or vessel having a retention pocket to hold one or more beneficial agents in the form of granulations or capsules therein so that when liquid flows over the retention pocket, the beneficial agent is released into the liquid and ingested.

Hot liquid herbal tea beverages have also been used for centuries to treat a variety of ailments. These beverages are typically prepared by brewing the leaves, stems, or roots of plants known to contain therapeutically active compounds. For example, menthol derived from peppermint leaves and ephedrine from Ma Huang/ephedra plants have been used as decongestants. Sennosides A and B derived from senna leaves have been used as laxatives. The brew produced from these plants, however, is often foul tasting and offensive to the drinker. Furthermore, the delivery of the active ingredient is imprecise because the active ingredient must be leached from the plant material, which can lead to under- or over-dosing of the active ingredient.

Although these herbal tea beverages are used around the world for their therapeutic effects, lack of dosage uniformity has typically made this method unsuitable for use as a regulated pharmaceutical preparation. Without wishing to be bound by any particular theory, when combining a pharmaceutical agent with tea leaves, a portion of the active ingredient may be absorbed or adsorbed by the tea leaves prior to steeping the tea, affecting the potency of the pharmaceutical agent.

Powdered pharmaceutical preparations containing active ingredients, sweeteners and flavors, which are dissolved in hot water and consumed as a hot liquid medication, are commercially available. These products typically contain acetaminophen, chlorpheniramine maleate, pseudophendrine hydrochloride, and dextromethorphan hydrobromide and are used to provide temporary relief of the symptoms typically associated with the cold and flu. Since the active ingredient is in powdered form that dissolves in hot water, the dosing problems associated with herbal teas are obviated. These hot liquid medications have, however, found limited acceptance in the marketplace because they often have an artificial taste.

Despite these developments, there remains a need for a palatable, easy method for administering medications in proper dosage amounts for those who prefer not to or are not able to swallow a pill. In particular, there is a need for a medicated coating on a filter bag able to deliver at least one pharmaceutical active, supplemental nutrient, or other beneficial agent.

SUMMARY OF THE INVENTION

The present invention is directed to a filter bag for oral administration of medication including a therapeutically effective amount of at least one medicinal agent, wherein the filter bag is formed of at least one sheet of porous material affixed together along margins to create sealed edges of the filter bag and to hold a beverage concentrate for infusion in a liquid, and wherein the at least one medicinal agent is applied to the at least one sheet of porous material prior to affixing the margins.

In one embodiment, the at least one medicinal agent is selected from the group consisting of a pharmaceutical active, a supplemental nutrient, a genetically derived material, a beneficial agent, and a combination thereof.

The pharmaceutical active may be selected from the group consisting of aspirin, a chemotherapy agent, an anti-neoplastic agent, a mood elevating drug, a depressant drug, an anti-diabetic drug, an anti-ulcer drug, a gastrointestinal drug, an infertility drug, a fertility drug, a hormone, an erectile dysfunction agent, an anti-inflammatory drug, a coagulation drug, an anti-coagulent drug, an anti-platelet agent, an ace inhibitor, a cardiovascular conditioning drug, a cholesterol reducing agent, a lipid reducing agent, an antihistamine drug, an anti-infective agent, an autonomic drug, a central nervous system agent, a smooth muscle relaxant, an antitussive agent, a mucolytic agent, and a combination thereof.

The supplemental nutrient may be selected from the group consisting of eucalyptus, glutamine, arginine, a fermentable dietary fiber, a non-fermentable dietary fiber, a phytochemical, an anti-oxidant, a mineral, an amino acid, an oligosaccharide, a short chain fatty acid, a pyruvate precursor, a pyruvyl-amino acid, an ester, a salt, a structured lipid, d-chiroinositol, lactoferrin, a marine oil, an ascorbic acid, and a combination thereof.

The beneficial agent may be selected from the group consisting of a probiotic, an enzyme, an electrolytic agent, a caloric agent, a water balance agent, a rehydration solution, a diagnostic agent, a vitamin, and a combination thereof.

The filter bag of the present invention may be used in hot or cold liquids. In one embodiment, the agent solubilizes when in contact with a liquid. The agent is preferably dispersed in a predetermined dosage amount into the liquid.

In one embodiment, the at least one medicinal agent is disposed between two layers of the at least one sheet of porous material. In another embodiment, the at least one medicinal agent is present in a mixture with a drug releasing element and the mixture is applied to the at least one sheet of porous material. In yet another embodiment, the at least one medicinal agent is disposed between the at least one sheet of porous material and a layer including a drug releasing element, preferably gelatin. The gelatin preferably dissolves when in contact with the liquid and releases the at least one medicinal agent into the liquid.

In one embodiment, the at least one medicinal agent is mixed with at least one enzymatically active material. In another embodiment, the at least one medicinal agent is present in a mixture including a temperature releasing agent. In yet another embodiment, the at least one medicinal agent is present in a mixture including a degradable material to provide a prolonged shelf life for the medicament. In still another embodiment, the at least one medicinal agent is present in a mixture including a flavor producing or reducing agent.

The at least one sheet of porous material is preferably selected from the group consisting of reinforced paper, knitted material, woven material, fibrous material, and a combination thereof.

In one embodiment, the filter bag holds a beverage concentrate selected from the group consisting of tea leaves, powdered tea, powdered milk, apple cider, powdered soup, hot cocoa, and instant coffee.

The present invention is also directed to a filter paper for oral administration of medication including a therapeutically effective amount of at least one medicinal agent selected from the group consisting of a pharmaceutical active, a supplemental nutrient, a genetically derived material, a beneficial agent, and a combination thereof, wherein the filter paper is formed of at least one sheet of porous material, and wherein the at least one medicinal agent is applied to the at least one sheet of porous material thereby producing a coated filter paper.

The coated filter paper preferably further includes a drug releasing layer to protect the at least one medicinal agent during storage.

The present invention is also directed to a method of making a medicinally coated filter bag including the steps of providing a first filter bag layer of porous material, applying a therapeutically effective amount of at least one medicinal agent selected from the group consisting of a pharmaceutical active, a supplemental nutrient, a genetically derived material, a beneficial agent, and a combination thereof to the first filter bag layer thereby producing a coated layer, and forming a pouch by sealing together margins of the porous material to form closed edges of the filter bag.

In one embodiment, the method further includes the steps of providing a second filter bag layer of porous material, and laying the second filter bag layer on top of the coated layer.

In another embodiment, the method further includes the steps of providing a gelatin coating and applying the gelatin coating to the coated layer.

In still another embodiment, the method further includes the steps of providing a beverage concentrate selected from the group consisting of tea leaves, powdered tea, powdered milk, apple cider, powdered soup, hot cocoa, and instant coffee and inserting the beverage concentrate into the pouch prior to sealing at least one edge of the filter bag.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

The present invention is directed to device and method for medicament delivery. In particular, the invention relates to a filter bag coated with at least one medicament and methods for making the coated filter bag. The medicament is never directly mixed with the tea leaves or powdered beverage concentrate that may be contained in the pouch of the filter bag, but is instead directly incorporated into the filter bag material prior to converting the filter bag material into a pouch. The medicament solubilizes when in contact with liquid and is dispersed in the proper dosage amount into the liquid for oral consumption. The present invention advantageously allows for a palatable, easy method for administering medicaments in proper dosage amounts for those who prefer not to or are not able to swallow a pill.

As used herein, "filter bag" is any self-contained pouch constructed to hold a beverage concentrate. An example of a filter bag of the invention is a tea bag, instant coffee bag, or the like.

The medicament used for coating the filter bag material is present in a therapeutically effective amount and may include pharmaceutical actives, supplemental nutrients, genetically derived materials, other beneficial agents, or combinations thereof. As used herein, "therapeutically effective amount" is an amount that produces the desired therapeutic response upon oral administration, and can be readily determined by one of ordinary skill in the art. In determining such amounts, the particular medicament being administered, the bioavailability characteristics of the medicament, the dose regime, the age and weight of the intended recipient, and other factors should be considered.

Pharmaceutical actives suitable for use in the coating include, but are not limited to, aspirin, cancer reducing agents, such as chemotherapy agents and anti-neoplastic agents, mood elevating drugs, depressant drugs, anti-diabetic drugs, anti-ulcer drugs, gastrointestinal drugs, such as antacids, infertility and fertility drugs, hormones, erectile dysfunction agents such as sildenafil citrate, anti-inflammatory drugs, blood formation and coagulation drugs, anticoagulent drugs, anti-platelet agents, ace inhibitors, cardiovascular conditioning drugs, cholesterol reducing agents, lipid reducing agents, antihistamine drugs such as $H_2$ blockers, anti-infective agents, such as antibiotics, antivirals and urinary tract anti-infectives, autonomic drugs and central nervous system agents such as adrenergic agents and skeletal muscle relaxants, smooth muscle relaxants, antitussive agents, and expectorant and mucolytic agents.

Suitable supplement nutrients include, but are not limited to, eucalyptus, glutamine, arginine, fermentable and non-fermentable dietary fibers, phytochemicals, anti-oxidants, minerals such as traces of selenium, chromium, molybdenum, zinc, and copper, electrolytes, gold compounds, combinations of amino acids, oligosaccharides such as fructo-oligosaccharides, short chain ($C_3$–$C_4$) fatty acids, pyruvate precursors in the form of pyruvamide, or pyruvyl-amino acids, such as, pyruvyl-glycine, pyruvyl-alanine, pyruvyl-leucine, pyruvyl-valine, pyruvyl-sarcosamine and their amides, esters and salts, structured lipids, d-chiroinositol, lactoferrin, marine oils and ascorbic acid.

As used herein, a "beneficial agent" is an ingredient that is, or is believed to be, nutritionally or pharmaceutically important to the patient, or is otherwise medically important. Suitable beneficial agents include, but are not limited to probiotics, enzymes, electrolytic, caloric, and water balance agents, rehydration solutions and diagnostic agents such as an opaquing agent, that may be orally administered in the medium of a liquid for drinking having a viscosity in the range of about 1 to about 300 centipoises. Each beneficial agent that is to be added in a physiologically effective or diagnostically detectable amount.

Figure 1:
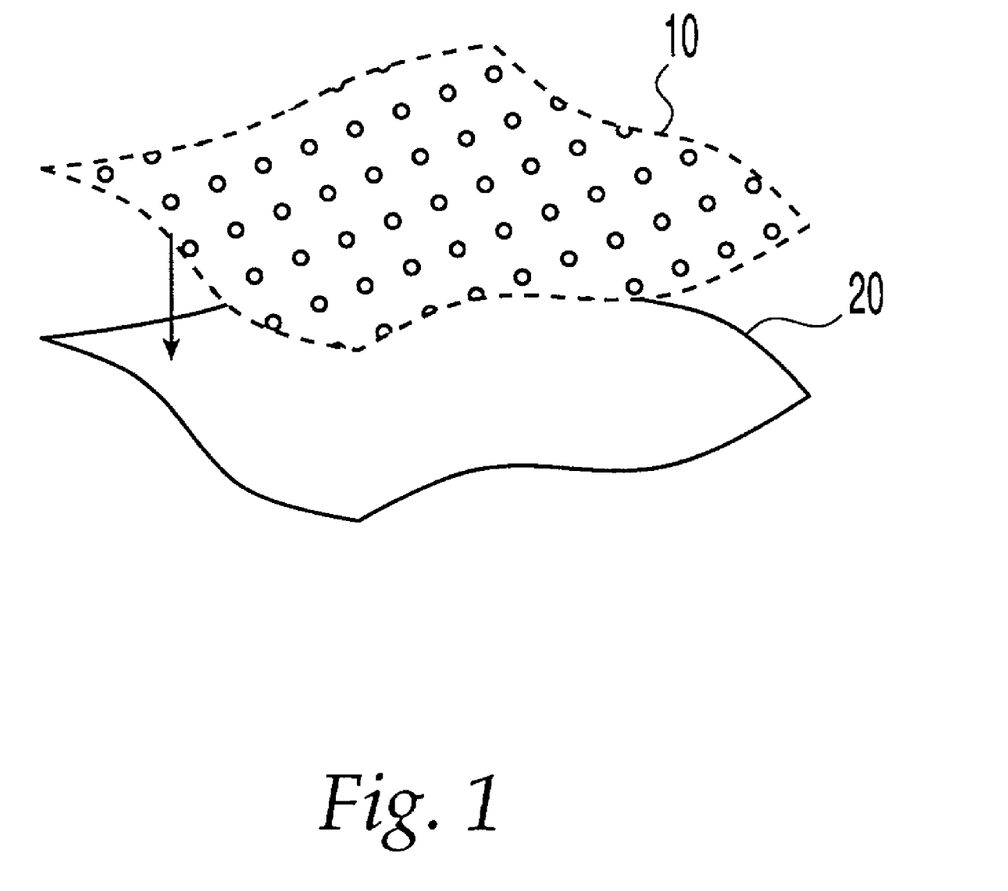
FIG. 1 is the coated filter bag material according to an embodiment of the present invention.

As shown in FIG. 1, the medicament 10 can be uniformly coated or loaded on top of the inside or the outside surface of the filter bag material 20. In another embodiment, illustrated in FIG. 2, the medicament 10 is sandwiched in between a lower filter bag material layer 30 and an upper filter bag material layer 40. At least one medicament is applied to the filter bag material, but multiple compatible medicaments may be included in the same filter bag material.

Figure 3:
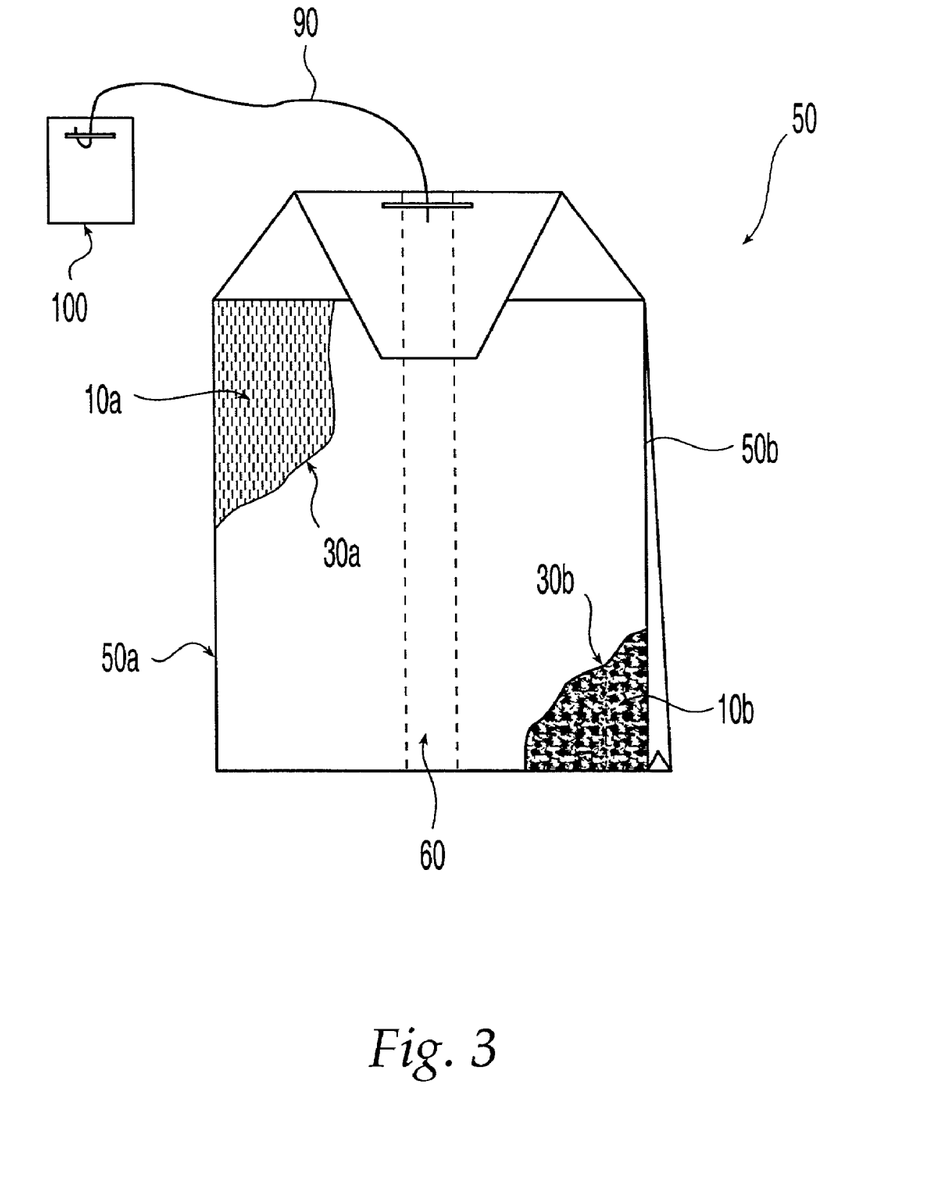
FIG. 3 is a perspective view showing a dual compartment filter bag according to one embodiment of the present invention.

The filter bag may also be constructed with dual compartments each of which are coated with a different, but compatible medicinal composition. The dual compartment filter bag may include a single layer of filter bag material coated with the medicament, or multiple layers sandwiching the medicaments. FIG. 3 shows a dual compartment filter bag 50 with a first medicament 10a included in the first half 50a of the filter bag 50, sandwiched between a lower filter bag material layer 30a and an upper filter bag material layer 40a (not shown) and a second medicament 10b coating the second half 50b of the filter bag 50, also sandwiched between a lower filter bag material layer 30b and a an upper filter bag material layer 40b (not shown). A seam 60 joins the two halves 50a, 50b to form a filter bag 50 having two medicaments.

Figure 2:
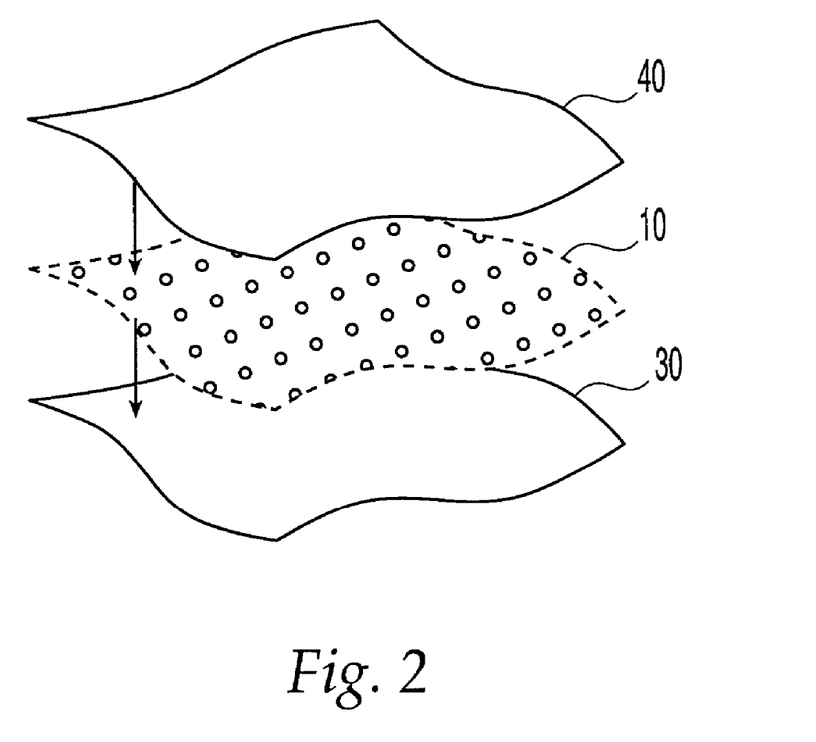
FIG. 2 is the coated filter bag material according to another embodiment of the present invention.
Figure 4:
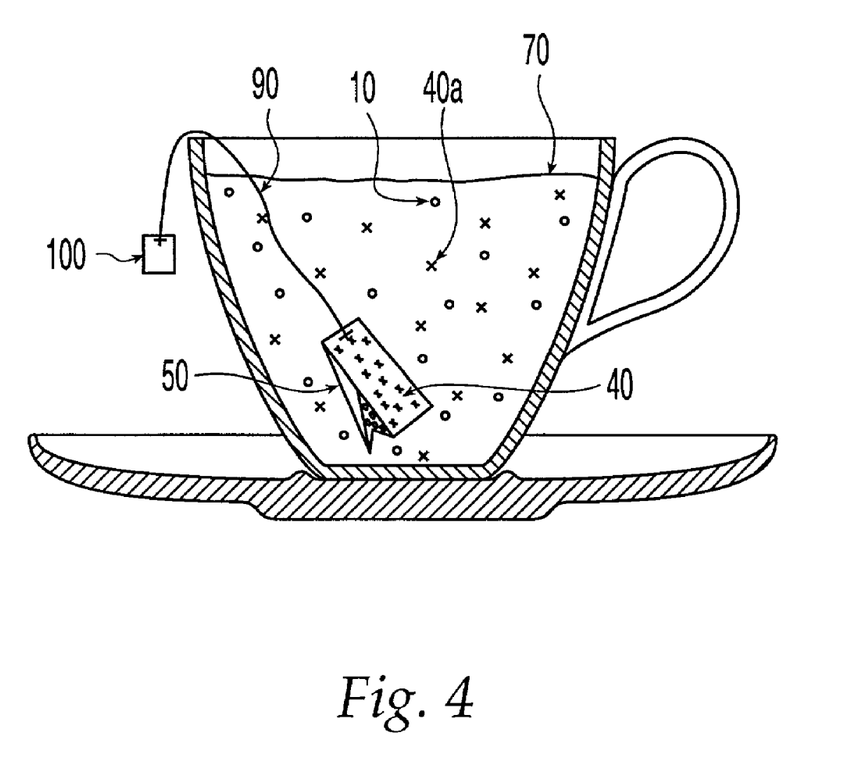
FIG. 4 is a side cross-sectional view of a cup showing the filter bag according to the present invention attached thereto.

In one embodiment, a drug releasing element, such as gelatin, may be impregnated on the surface of the filter bag material after applying the medicament, thus sandwiching the medicament between the gelatin layer and the filter bag material. This concept is shown in FIG. 2, wherein upper filter bag material layer 40 is substituted with gelatin instead of the layer of filter bag material. The gelatin coating may act to keep the medicament stable and protected from moisture or deleterious airborne substances. Upon immersion in a liquid 70, the gelatin layer 40 breaks down into gelatin particles 40a, which dissolve into the liquid 70, and the medicament 10 is released into the liquid 70, as depicted in FIG. 4. The gelatin may be applied to the outside or inside surface of the filter bag after applying the medicated coating. In another embodiment, the gelatin and the medicament are premixed and applied to the filter bag together such that the medicament is embedded within the gelatin layer.

It is recommended that the gelatin coating utilized in the present invention for coating the filter bag surface be provided in an aqueous solution having a gelatin concentration of from about 20 weight percent to about 40 weight percent gelatin. The apparent viscosity of this gelatin solution is recommended to be from about 800 to about 1000 centipoise as measured at about 40° C. to about 50° C. on a Brookfield viscometer. The preferred gelatin for the practice of the present invention is a mixture including from about 60 weight percent to about 80 weight percent of bone gelatin and from about 40 weight percent to about 20 weight percent of pork gelatin on a dry weight basis with the total weight percent of the dry components totaling 100 weight percent. The currently preferred gelatin mixture is 70 weight percent bone gelatin and 30 weight percent pork gelatin. Any color gelatin solutions may be utilized, but it is preferred that the gelatin be colorless so as to not interfere with the natural color of the tea leaves.

Enzymatically active materials may also be mixed with the medicaments used to coat the filter bag material so as to improves or slow down the rate of dissolution when in contact with liquid. The medicament may also be mixed with a temperature releasing agent so that the medicament will only dissolve when the liquid is at a certain temperature. Degradable materials, such as synthetic, biological, or genetically derived materials, may also be mixed with the medicament prior to coating so as to preserve the medicament and thus, extend its shelf life.

The coated filter bags of the present invention may also include a flavor-reducing or producing element. For example, a filter bag may be coated with a medicinal agent having an inherent foul or bitter taste, but supplementation with a compatible flavor producing coating will help to mask the foul taste of the medicament. Generally the flavor-producing element contains at least one sweetening agent in addition to the flavoring element. The flavoring element and sweetening agent should be of a type and amount so as not to interfere with the beneficial active ingredient of the medicament, and also to meet the preferences dictated by the intended consumer, e.g., adult user or pediatric user Sugar sweetening agents for use in the coated filter bag may include sugars, monosaccharides, disaccharides, and polysaccharides. Suitable sugars for use in the coated filter bag include, but are not limited to, xylose, ribose, glucose, mannose, galactose, fructose, dextrose, sucrose, maltose, partially hydrolyzed starch or corn syrup solids and sugar alcohols, such as sorbitol, xylitol, mannitol, glycerine, and combinations thereof.

Water soluble artificial sweeteners may also be employed in the place of or in addition to the aforementioned sugar sweeteners. Examples of suitable artificial sweeteners include, but are not limited to, aspartame, sucralose, cyclamates, saccharin, and mixtures thereof.

The coated filter bag of the present invention may also include various vitamins and minerals. Suitable vitamins for use in the coated filter bag include, but are not limited to, vitamins of the B-complex group, Vitamin C in the form of ascorbic acid, and mixtures thereof. The presence of these vitamins and minerals are present in the coated filter bag at levels in accordance with the recommended doses for the intended recipients.

Various other pharmaceutically acceptable excipients may be included, such as preservatives and coloring agents.

The filter bag material is preferably a fibrous and highly porous paper, reinforced paper, knitted or woven material. The filter bag material usually comes on a roll on which a continuous strip of porous filter bag material is wound. The strip is fed into a machine for making filter bags, wherein a series of feed rollers controls the tension of the feed. An example of such a machine, one for making tea bags, is described in U.S. Pat. No. 5,871,789, which is incorporated in its entirety by reference herein. The medicament can be uniformly coated or loaded on the filter bag material prior to winding onto the roll. In another embodiment, the filter bag material is coated on the conveyor belt prior to conversion into a pouch.

Figure 5:
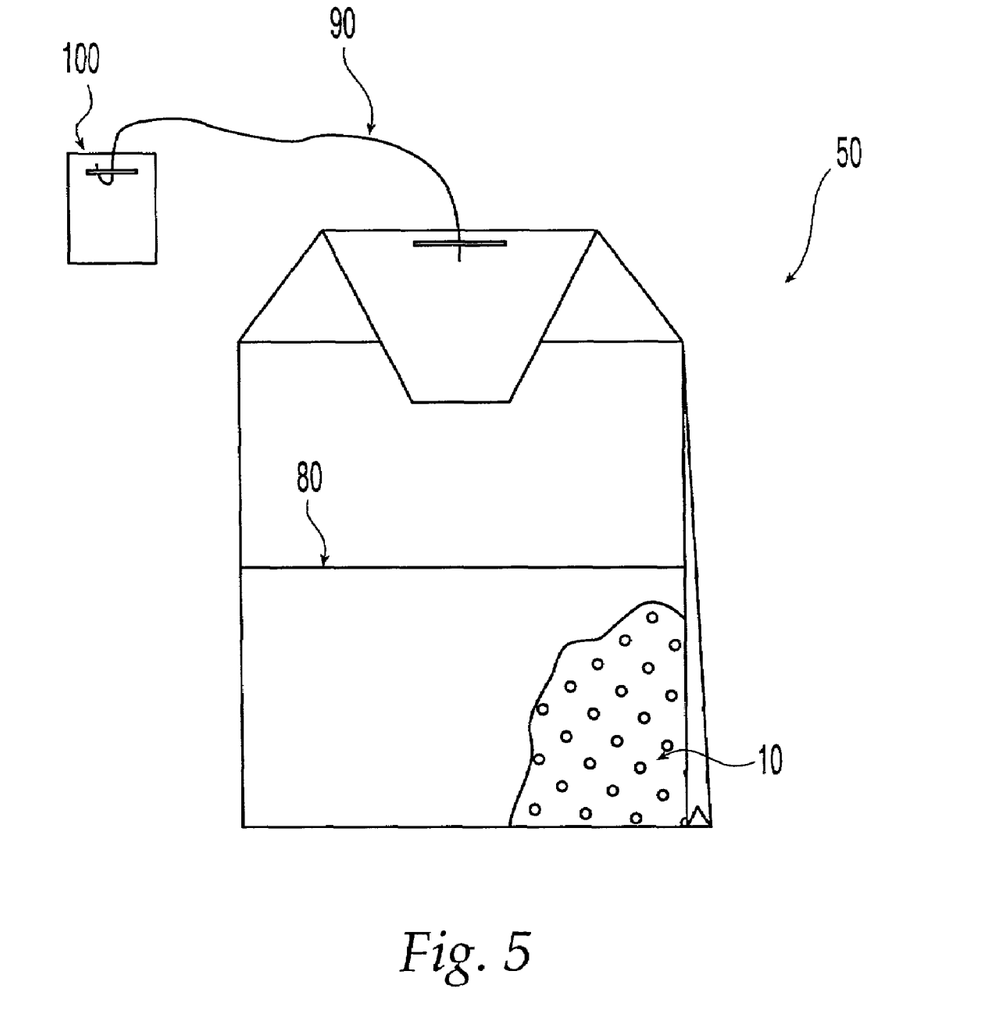
FIG. 5 is a perspective view showing a filter bag according to an embodiment of the present invention.

Once the coated filter bag material is converted into a pouch by any method known to those of ordinary skill in the art, tea leaves, tea powder, or other powdered beverage concentrates 80 can be inserted into the filter bag 50 and sealed. The filter bag 50, shown in FIG. 5, may include a thread 90 used for holding during immersion in liquid and fastened to the upper edge of the filter bag and to a tag 100 used for picking up the filter bag 50 itself.

In one embodiment, the filter bag does not contain tea leaves or a beverage concentrate, but instead is left unfilled so that it may be used in liquids other than water. For example, powdered food and drink concentrates added to water such as powdered milk, hot cocoa, soup, instant tea, and instant coffee, may be prepared as usual. The coated filter bag of the invention may then be added to allow uniform dispersion of the medicament in the prepared liquid or liquid-type food. This method of delivery may also be used with canned food concentrates.

In another embodiment, the porous material is not converted into a pouch after application of the medicinal coating, but instead left as a flat sheet of coated porous material to be inserted into a liquid. The sheet of porous material in this embodiment acts only to retain the medicament for storage until submerged into liquid and subsequently released. The sheet may include a thread used for holding during immersion in liquid and fastened to any edge and to a tag used for maneuvering the sheet into and out of the liquid. The sheet may be single-ply, double-ply, or more, but in this embodiment, is not capable of holding a beverage concentrate.

When the coated filter bag is added to a liquid, cold or hot, a liquid beverage is formed or supplemented with the medicament. The medicament, whether impregnated into the filter bag protected by a drug releasing element or independently impregnated into the filter bag, must be dispersible in the medium of the liquid for ingesting during an interval just prior to or during feeding, in order to meet the objectives of the invention. Since the medicament is dependently or independently impregnated directly into the filter bag material, instead of incorporated with the tea leaves or beverage concentrate, and does not contain plant materials, e.g., leaves, stems, or roots, normally found in herbal tea products, the medicament is accurately delivered to the user.

It is to be understood that the invention is not to be limited to the exact configuration as illustrated and described herein. The embodiments discussed in the Detailed Description of the Invention are not intended to limit the invention. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A filter bag for oral administration of medicament comprising:
    at least one sheet of porous material having a therapeutically effective amount of at least one medicinal agent incorporated therein, wherein the said medicinal agent is incorporated into porous material prior to the formation of said filter bag the at least one sheet of porous material forming a sealed bag having a beverage concentrate therein separate from the medicinal agent;
    wherein the therapeutically effective amount of the at least one medicinal agent produces a therapeutic response upon oral administration,
    wherein the at least one medicinal agent is a pharmaceutical active selected from the group consisting of aspirin, sildenafil citrate, a coagulation drug, an anti-coagulent drug, an anti-platelet agent, an ace inhibitor, a cholesterol reducing agent, a lipid reducing agent, and
    wherein the medicinal agent is incorporated into the at least one sheet of porous material without directly mixing with the beverage concentrate.

2. The filter bag of claim 1, wherein the filter bag is adapted for use in cold or hot liquids.

3. The filter bag of claim 1, wherein the agent is adapted to solubilize when in contact with a liquid.

4. The filter bag of claim 3, wherein the agent is adapted to be dispersable in a predetermined dosage amount into the liquid.

5. The filter bag of claim 1, wherein the at least one medicinal agent is present in a mixture with a drug releasing element and the mixture is applied to the at least one sheet of porous material.

6. The filter bag of claim 1, wherein the drug releasing element is gelatin.

7. The filter bag of claim 6, wherein the gelatin is dissolvable when in contact with the liquid to release the at least one medicinal agent into the liquid.

8. The filter bag of claim 1, wherein the at least one medicinal agent is mixed with at least one enzymatically active material.

9. The filter bag of claim 1, wherein the at least one medicinal agent is present in a mixture comprising a temperature releasing agent.

10. The filter bag of claim 1, wherein the at least one medicinal agent is resent in a mixture comprising a degradable material adapted to provide a prolonged shelf life for the medicament.

11. The filter bag of claim 1, wherein the at least one medicinal agent is present in a mixture comprising a flavor producing or reducing agent.

12. The filter bag of claim 1, wherein teat least one sheet of porous material is selected from the group consisting of reinforced paper, knitted material, woven material, fibrous material, and a combination thereof.

13. The filter bag of claim 1, wherein the filter bag holds a beverage concentrate selected from the group consisting of tea leaves, powdered tea, powdered milk, apple cider, powdered soup, hot cocoa, and instant coffee.

14. A filter bag for oral administration of medicament comprising:
    at least one sheet of porous material forming a sealed bag comprising first and second compartments disposed in side by side relation to one another;
    a beverage concentrate disposed in one of the compartments; and
    a therapeutically effective amount of at least one medicinal agent incorporated into the porous material wherein the said medicinal agent is incorporated into porous material prior to the formation of said filter bag, wherein the therapeutically effective amount of the at least one medicinal agent produces a therapeutic response upon oral administration,
    wherein the medicinal agent differs in composition from the beverage concentrate and the medicinal agent and the beverage concentrate are not directly mixed and wherein the medicinal agent is aspirin or sildenafil citrate.

15. The filter bag of claim 14, further comprising at least one enzymatically active material.

16. The filter bag of claim 14, further comprising a temperature releasing agent.

17. The filter bag of claim 14, further comprising a flavor producing or reducing agent.

18. The filter bag of claim 14, wherein the at least one sheet of porous material is selected from the group consisting of reinforced paper, knitted material, woven material, fibrous material, and a combination thereof.

19. The filter bag of claim 14, wherein the beverage concentrate comprises tea concentrate.

* * * * *

UNITED STATES PATENT AND TRADEMARK OFFICE
CERTIFICATE OF CORRECTION

PATENT NO.      : 7,090,858 B2
APPLICATION NO. : 09/924540
DATED           : August 15, 2006
INVENTOR(S)     : Swaminathan Jayaraman

It is certified that error appears in the above-identified patent and that said Letters Patent is hereby corrected as shown below:

Column 8, line 16 change "resent" to --present--

Column 8, line 44 change "teat" to -- the at--

Signed and Sealed this

Twenty-sixth Day of December, 2006

JON W. DUDAS
*Director of the United States Patent and Trademark Office*